(12) United States Patent
Liu et al.

(10) Patent No.: US 12,702,414 B2
(45) Date of Patent: Aug. 11, 2026

(54) SURGICAL STAPLER

(71) Applicants: EZISURG MEDICAL CO., LTD., Shanghai (CN); EZISURG (SUZHOU) MEDICAL CO., LTD., Jiangsu (CN)

(72) Inventors: Yang Liu, Shanghai (CN); Chuangang Tang, Shanghai (CN); Guang Yang, Shanghai (CN); Honglin Nie, Shanghai (CN)

(73) Assignees: EZISURG MEDICAL CO., LTD., Shanghai (CN); EZISURG (SUZHOU) MEDICAL CO., LTD., Jiangsu (CN)

( * ) Notice: Subject to any disclaimer, the term of this patent is extended or adjusted under 35 U.S.C. 154(b) by 0 days.

(21) Appl. No.: 19/220,755

(22) Filed: May 28, 2025

(65) Prior Publication Data

US 2025/0366854 A1 Dec. 4, 2025

(30) Foreign Application Priority Data

May 31, 2024 (CN) ......................... 202410696479.0

(51) Int. Cl.
*A61B 17/00* (2006.01)
*A61B 17/072* (2006.01)

(52) U.S. Cl.
CPC .................. *A61B 17/07207* (2013.01); *A61B 2017/00367* (2013.01); *A61B 2017/00477* (2013.01); *A61B 2017/00862* (2013.01)

(58) Field of Classification Search
CPC .... A61B 17/07207; A61B 2017/00367; A61B 2017/00477; A61B 2017/00862; A61B 1/00; A61B 17/068; A61B 19/2203; A61B 2019/2238
USPC ........................................... 227/176.1, 177.1
See application file for complete search history.

(56) References Cited

U.S. PATENT DOCUMENTS

2006/0199999 A1* 9/2006 Ikeda .................... A61B 34/71 600/141
2014/0291383 A1* 10/2014 Spivey ............ A61B 17/07207 227/177.1

FOREIGN PATENT DOCUMENTS

CN 116747025 A * 9/2023 ............ A61B 34/30

* cited by examiner

*Primary Examiner* — Jacob A Smith
(74) *Attorney, Agent, or Firm* — Fox Rothschild LLP

(57) ABSTRACT

A surgical stapler is provided. The surgical stapler includes: an intermediate connecting member, an end effector assembly, a first bending tension member and a second bending tension member; the first bending tension member is configured to pass through the first channel to connect to the end effector assembly; the second bending tension member is configured to pass through the second channel to connect to the end effector assembly; a first protruding structure is provided on a side of the first channel close to the second channel; when the second bending tension member is forced to pull the end effector assembly to bend along a second direction, the first bending tension member passively contacts the first protruding structure, generating additional tension force. The present disclosure prevents the first bending tension member from loosening during the surgical procedure, thereby reducing traction or abrasion to the patient's tissue.

9 Claims, 12 Drawing Sheets

SURGICAL STAPLER

CROSS-REFERENCE TO RELATED APPLICATIONS

The disclosure is based upon and claims priority to Chinese Patent Application No. 202410696479.0, filed on May 31, 2024, the entire contents of which are incorporated herein by reference.

TECHNICAL FIELD

The present disclosure relates to surgical instrument technology, in particular to a surgical stapler.

BACKGROUND

Generally, a surgical stapler includes a handle, a bending control mechanism, an end effector assembly, and the like. During the surgical procedure, the surgeon uses the stapler to open or bend the end effector assembly via the handle, thereby performing stapling and cutting of a patient's tissue. The inventor of the present disclosure has found that, under a firing force condition, the bending control mechanism of existing staplers may cause the end effector assembly to swing, thereby causing traction or abrasion to the patient's tissue and increasing the risk of the surgical procedure.

SUMMARY

To solve the problems in the prior art, the present disclosure aims to provide a surgical stapler including an intermediate connecting member, an end effector assembly, a first bending tension member, and a second bending tension member; wherein the intermediate connecting member includes a first channel and a second channel; the first bending tension member is configured to pass through the first channel to connect to the end effector assembly; the second bending tension member is configured to pass through the second channel to connect to the end effector assembly; a first protruding structure is provided on a side of the first channel close to the second channel; when the second bending tension member is forced to pull the end effector assembly to bend along a second direction, the first bending tension member passively contacts the first protruding structure, expanding along a first direction to generate additional tension force.

Optionally, a second protruding structure is provided on a side of the second channel close to the first channel; when the first bending tension member is forced to pull the end effector assembly to bend along the first direction, the second bending tension member passively contacts the second protruding structure, expanding along the second direction to generate additional tension force.

Optionally, when the end effector assembly is not bent, the first bending tension member contacts the first protruding structure, expanding along the first direction to generate additional tension force; the second bending tension member contacts the second protruding structure, expanding along the second direction to generate additional tension force.

Optionally, the tension force generated by the first bending tension member and the tension force generated by the second bending tension member are kept in balance.

Optionally, the intermediate connecting member is a one-piece structure; the first channel or the second channel is respectively continuous; the side of the first channel close to the second channel is integrally formed as the first protruding structure; the side of the second channel close to the first channel is integrally formed as the second protruding structure.

Optionally, the intermediate connecting member is a multi-piece assembly structure; the first channel includes a plurality of first sub-channels; the second channel includes a plurality of second sub-channels; a side of any of the first sub-channels close to the second sub-channels is provided with the first protruding structure; a side of any of the second sub-channels close to the first sub-channels is provided with the second protruding structure.

Optionally, when the first bending tension member is forced to pull the end effector assembly to bend along the first direction, the first bending tension member is positioned on a side of the first channel away from the second channel; when the second bending tension member is forced to pull the end effector assembly to bend along the second direction, the second bending tension member is positioned on a side of the second channel away from the first channel.

Optionally, when the first bending tension member is forced to pull the end effector assembly to bend along the first direction, an amount of deformation of the first bending tension member is less than an amount of deformation of the second bending tension member; when the second bending tension member is forced to pull the end effector assembly to bend along the second direction, the amount of deformation of the second bending tension member is less than the amount of deformation of the first bending tension member.

Optionally, the intermediate connecting member is elastic; when the end effector assembly bends along the first direction, the intermediate connecting member is compressed on a side facing the first direction to provide supporting force and stretches on a side facing the second direction; when the end effector assembly bends along the second direction, the intermediate connecting member is compressed on the side facing the second direction to provide supporting force and stretches on the side facing the first direction.

Optionally, the surgical stapler further includes a handle assembly; wherein the handle assembly includes a drive assembly; the first bending tension member and the second bending tension member are respectively connected to the drive assembly; the drive assembly is configured to tighten the first bending tension member and loosen the second bending tension member, thereby driving the end effector assembly to bend along the first direction; the drive assembly is configured to tighten the second bending tension member and loosen the first bending tension member, thereby driving the end effector assembly to bend along the second direction.

The present disclosure provides a surgical stapler wherein the first protruding structure is provided on a side of the first channel that is close to the second channel. The second bending tension member tightens when it is forced to pull the end effector assembly to bend along the second direction. At the same time, the first bending tension member passively contacts the first protruding structure, expanding along the first direction to generate additional tension force. Such a configuration prevents the first bending tension member from loosening during the surgical procedure, which could cause the end effector assembly to swing, thereby reducing traction or abrasion to the patient's tissue.

REFERENCE NUMERALS

1000, surgical stapler; 11, handle assembly; 100, intermediate connecting member; 111, connecting portion; 112, left wing portion; 1121, first sub-channel; 113, right wing portion; 1131, second sub-channel; 120, knife holder channel; 130, first channel; 131, first protruding structure; 132, outer sidewall of the first channel; 140, second channel; 141, second protruding structure; 142, outer sidewall of the second channel; 200, end effector assembly; 210, anvil assembly; 220, staple cartridge assembly; 300, connecting tube; 400, first bending tension member; 500, second bending tension member; 600, articulated structure; 610, first connecting member; 620, second connecting member; 630, connecting shaft; D1, first direction; D2, second direction; A, third direction; Z, central axis of the intermediate connecting member.

DETAILED DESCRIPTION

For better understanding and implementation, technical solutions in embodiments of the present disclosure will be described clearly and completely in conjunction with drawings in the embodiments of the present disclosure.

In the description of the present disclosure, it is to be noted that orientations or position relations indicated by terms such as “upper”, “lower”, “front”, “back”, “left”, “right”, “vertical”, “horizontal”, “top”, “bottom”, “inside”, “outside”, “far”, and “near” are based on the drawings. These orientations or position relations are intended only to facilitate and simplify the description of the present disclosure and not to indicate or imply that a device or element referred to must have such particular orientations or must be configured or operated in such particular orientations. Thus, these orientations or position relations are not to be construed as limiting the present disclosure.

Unless otherwise defined, all technical and scientific terms used herein have meanings the same as those commonly understood by those skilled in the art to which the present disclosure pertains. Terms used in the specification of the present disclosure are only used for describing embodiments and not intended to limit the present disclosure.

Figure 1:
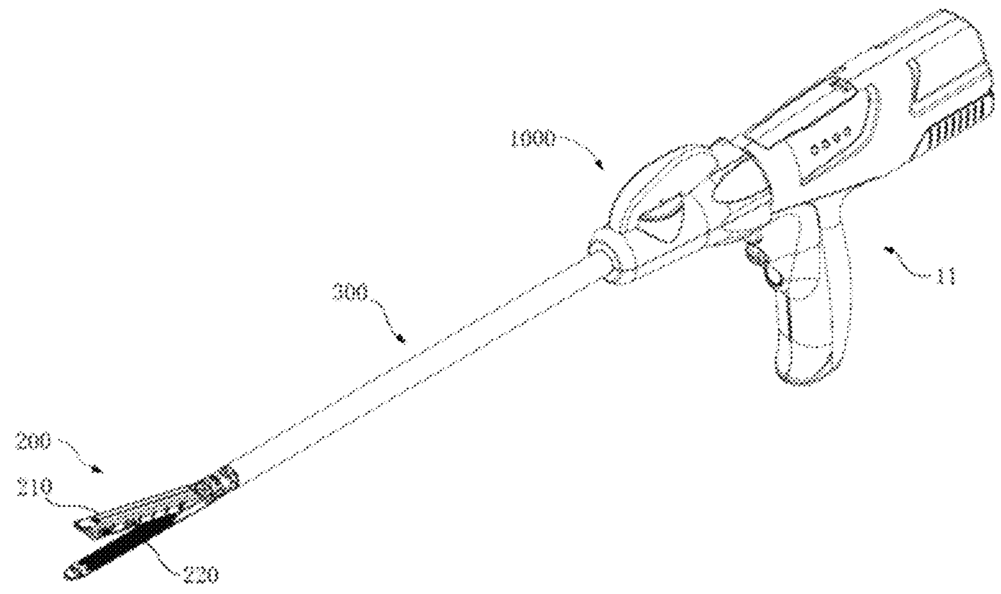
FIG. 1 is a perspective view of a surgical stapler according to an embodiment of the present disclosure.
Figure 2:
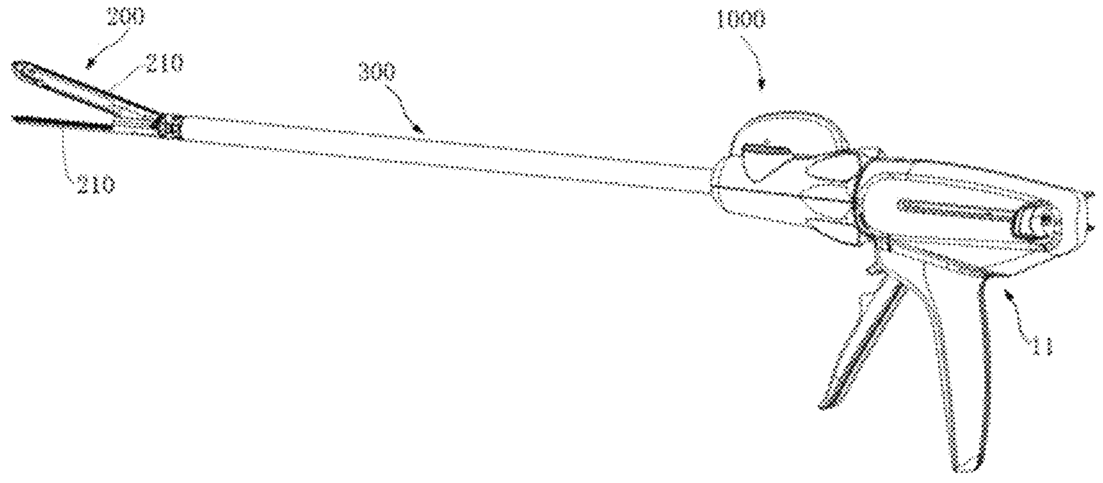
FIG. 2 is a perspective view of the surgical stapler according to another embodiment of the present disclosure.

As shown in FIG. 1 and FIG. 2, a surgical stapler 1000 includes an end effector assembly 200, a connecting tube 300, a handle assembly 11 and an intermediate connecting member 100. The handle assembly 11, the connecting tube 300, the intermediate connecting member 100 and the end effector assembly 200 are sequentially connected from proximal to distal, and the connecting tube 300 is articulated with the end effector assembly 200. The surgical stapler 1000 includes tension members positioned on left and right sides within its interior, and the handle assembly 11 includes a drive assembly, with one end of the left tension member connected to the drive assembly and the other end connected to the end effector assembly 200, and one end of a right tension member connected to the drive assembly and the other end connected to a control end, such that when the drive assembly moves, one of the left tension member and the right tension member tightens while loosening the other, thereby causing the end effector assembly 200 to bend. In existing designs, when the drive assembly rotates to one side, it tightens the left tension member while loosening the right tension member, causing the end effector assembly 200 to bend to the left. When the drive assembly rotates to the other side, it tightens the right tension member while loosening the left tension member, causing the end effector assembly 200 to bend to the right. Typically, in the prior art, the end effector assembly 200 is a jaw structure that includes an anvil assembly 210, a staple cartridge assembly 220, a knife holder, and the like. The end effector assembly 200 can be clamped to staple and cut the patient’s tissue. As shown in FIG. 1, the surgical stapler 1000 can be fired by a motor. As shown in FIG. 2, the surgical stapler 1000 can be fired manually.

It is found that, since the left tension member serves as a tightened structure, it remains in a tensioned state, while the right tension member is untightened, it becomes relatively loose after the end effector assembly 200 bends, thereby causing the end effector assembly to swing, which results in traction or abrasion of the patient’s tissue.

As shown in FIG. 1 to FIG. 6, the present disclosure provides a surgical stapler 1000 including an intermediate connecting member 100, an end effector assembly 200, a first bending tension member 400, and a second bending tension member 500. The intermediate connecting member 100 includes a first channel 130 and a second channel 140. The first bending tension member 400 is configured to pass through the first channel 130 to connect to the end effector assembly 200. The second bending tension member 500 is configured to pass through the second channel 140 to connect to the end effector assembly 200. A first protruding structure 131 is provided on a side of the first channel 130 close to the second channel 140. When the second bending tension member 500 is forced to pull the end effector assembly 200 to bend along a second direction D2, the first bending tension member 400 passively contacts the first protruding structure 131, expanding along a first direction D1 to generate additional tension force.

It should be noted that the passive contact of the first bending tension member 400 with the first protruding structure 131 refers to a situation where, when the end effector assembly 200 bends along a second direction D2, the first bending tension member 400 is driven by the end effector assembly 200 to move toward the first protruding structure 131.

To better illustrate the present disclosure, the drawings indicate a first direction D1, a second direction D2, and a third direction A. The third direction A extends from a proximal end to a distal end, the first direction D1 extends from right to left, and the second direction D2 extends from left to right.

As shown in FIG. 4 to FIG. 9, the first bending tension member 400 is positioned on the left side, and the second bending tension member 500 is positioned on the right side. When the second bending tension member 500 is forced to pull the end effector assembly 200 to bend along a second direction D2 (from left to right), the first bending tension member 400 passively contacts the first protruding structure 131, causing the first bending tension member 400 to expand along a first direction D1 (from right to left) to generate additional tension force.

In the above solution, a first protruding structure 131 is provided on a side of the first channel 130 close to the second channel 140, increasing the deformation amount of the first bending tension member 400 contacting the first protruding structure 131, such that the first bending tension member 400 is tightened, thereby preventing the end effector assembly from swinging and reducing traction or abrasion to the patient's tissue. It should be noted that in the above situation, the second bending tension member 500 remains in a tensioned state due to external force.

In addition, the expansion of the first bending tension member 400 refers to a situation where, after the first bending tension member 400 contacts the first protruding structure 131, the first bending tension member 400 is lifted by the first protruding structure 131, increasing the amount of deformation of the first bending tension member 400, and thereby generating greater tension force.

Optionally, a second protruding structure 141 is provided on a side of the second channel 140 close to the first channel 130; when the first bending tension member 400 is forced to pull the end effector assembly 200 to bend along a first direction D1, the second bending tension member 500 passively contacts the second protruding structure 141, expanding along a second direction D2 to generate additional tension force.

It should also be noted that the passive contact of the second bending tension member 500 with the second protruding structure 141 refers to a situation where, when the end effector assembly 200 bends along a first direction D1, the second bending tension member 500 is driven by the end effector assembly 200 to move toward the second protruding structure 141.

In the above solution, a second protruding structure 141 is provided on a side of the second channel 140 close to the first channel 130, increasing the deformation amount of the second bending tension member 500 contacting the second protruding structure 141, such that the second bending tension member 500 is tightened, thereby preventing the end effector assembly from swinging and reducing traction or abrasion to the patient's tissue. It should be noted that in the above situation, the first bending tension member 400 remains in a tensioned state due to external force.

As shown in FIG. 4 to FIG. 9, when the first bending tension member 400 is forced to pull the end effector assembly 200 to bend along a first direction D1 (from right to left), the second bending tension member 500 passively contacts the second protruding structure 141, expanding along a second direction D2 (from left to right) to generate additional tension force.

In addition, the expansion of the second bending tension member 500 refers to a situation where, after the second bending tension member 500 contacts the second protruding structure 141, the second bending tension member 500 is lifted by the second protruding structure 141, increasing the amount of deformation of the second bending tension member 500, and thereby generating greater tension force.

The above solution provides a first protruding structure 131 on a side of the first channel 130 close to the second channel 140 and a second protruding structure 141 on a side of the second channel 140 close to the first channel 130, such that when the end effector assembly 200 bends, the first bending tension member 400 and the second bending tension member 500 passively contact the first protruding structure 131 and the second protruding structure 141, respectively, generating additional tension force. Such a configuration prevents the first bending tension member 400 or the second bending tension member 500 from loosening during the surgical procedure, which could cause the end effector assembly to swing, thereby reducing traction or abrasion to the patient's tissue.

As shown in FIG. 4 to FIG. 8, when the end effector assembly 200 is not bent, the first bending tension member 400 contacts the first protruding structure 131, expanding along a first direction D1 to generate additional tension force, and the second bending tension member 500 contacts the second protruding structure 141, expanding along a second direction D2 to generate additional tension force. Such a configuration prevents the situation during the surgical procedure where the first bending tension member 400 and the second bending tension member 500 loosen, causing the end effector assembly 200 to swing while remaining not bent, thereby reducing traction or abrasion to the patient's tissue.

As shown in FIG. 4 to FIG. 9, the tension force generated by the first bending tension member 400 remains balanced with the tension force generated by the second bending tension member 500. Specifically, when the second bending tension member 500 is forced to pull the end effector assembly 200 to bend along a second direction D2, the first bending tension member 400 passively contacts the first protruding structure 131, expanding along a first direction D1 to generate additional tension force. Under this condition, the tension force generated by the first bending tension member 400 and the tension force generated by the second bending tension member 500 are kept in balance. When the first bending tension member 400 is forced to pull the end effector assembly 200 to bend along a first direction D1, the second bending tension member 500 passively contacts the second protruding structure 141, expanding along a second direction D2 to generate additional tension force. Under this condition, the tension force generated by the first bending tension member 400 and the tension force generated by the second bending tension member 500 are kept in balance. When the end effector assembly 200 is not bent, the first bending tension member 400 contacts the first protruding structure 131, expanding along a first direction D1 to generate additional tension force, and the second bending tension member 500 contacts the second protruding structure 141, expanding along a second direction D2 to generate additional tension force. Under this condition, the tension force generated by the first bending tension member 400 and the tension force generated by the second bending tension member 500 are kept in balance. Thus, the first bending tension member 400 and the second bending tension member 500 remain in an equally tensioned state, preventing the end effector assembly 200 from swinging due to slight external forces, thereby reducing traction or abrasion to the patient's tissue.

Figure 10:
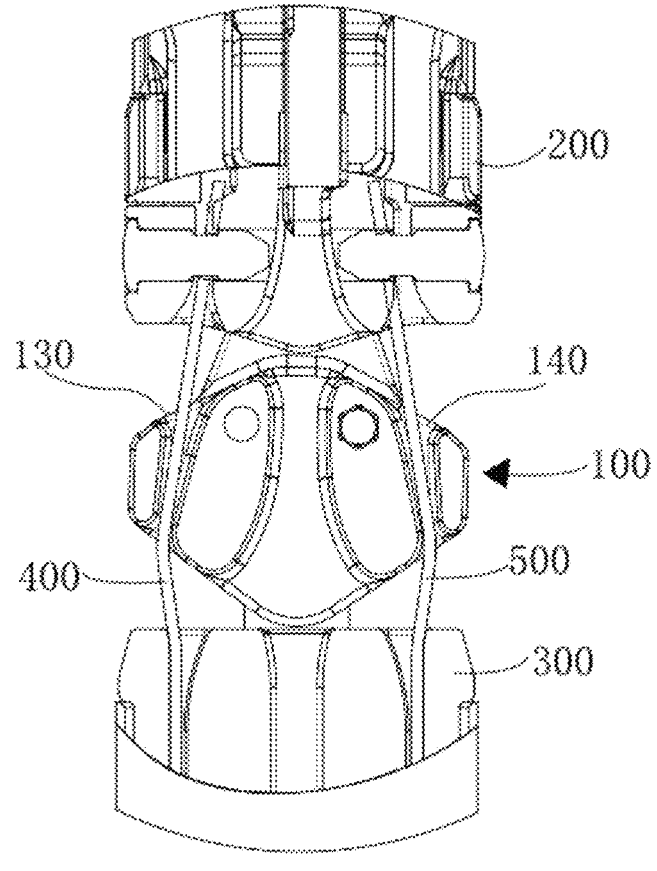
FIG. 10 is a partial cross-sectional view of the surgical stapler according to yet another embodiment of the present disclosure.

As shown in FIG. 10, the intermediate connecting member 100 is a one-piece structure, and the first channel 130 or the second channel 140 is respectively continuous. One side of the first channel 130 is integrally formed as the first protruding structure 131, and one side of the second channel 140 is integrally formed as the second protruding structure 141.

In the above solution, the intermediate connecting member 100 is configured as a one-piece structure to facilitate design and manufacturing. One side of the first channel 130 is integrally formed as the first protruding structure 131, increasing the contact area between the first protruding structure 131 and the first bending tension member 400, enabling the first bending tension member 400 to fully expand and generate sufficient additional tension force. One side of the second channel 140 is integrally formed as the second protruding structure 141, increasing the contact area between the second protruding structure 141 and the second bending tension member 500, enabling the second bending tension member 500 to fully expand and generate sufficient additional tension force.

As shown in FIG. 4 to FIG. 9, the intermediate connecting member 100 is a multi-piece assembly structure. The first channel 130 includes a plurality of first sub-channels 1121, and the second channel 140 includes a plurality of second sub-channels 1131. A side of any of the first sub-channels 1121 close to the second sub-channels 1131 is provided with the first protruding structure 131, and a side of any of the second sub-channels 1131 close to the first sub-channels 1121 is provided with the second protruding structure 141.

It should be noted that the second sub-channel 1131 is located to the right of the first sub-channel 1121, such that the side of the first sub-channel 1121 close to the second sub-channel 1131 is understood as the right side of the first sub-channel 1121. Correspondingly, the first sub-channel 1121 is located to the left of the second sub-channel 1131, such that the side of the second sub-channel 1131 close to the first sub-channel 1121 is understood as the left side of the second sub-channel 1131. In the above solution, gaps are provided between the multiple first sub-channels 1121 to form the first channel 130, and gaps are provided between the multiple second sub-channels 1131 to form the second channel 140. Such a configuration facilitates the intermediate connecting member 100 to cooperate with the end effector assembly 200 to deform during bending.

It should be noted that, to better guide the bending of the first bending tension member 400 and the second bending tension member 500, in some embodiments, the first protruding structure 131 of the first channel 130 is configured as a partially or entirely curved surface, and the second protruding structure 141 of the second channel 140 is configured as a partially or entirely curved surface.

Figure 6:
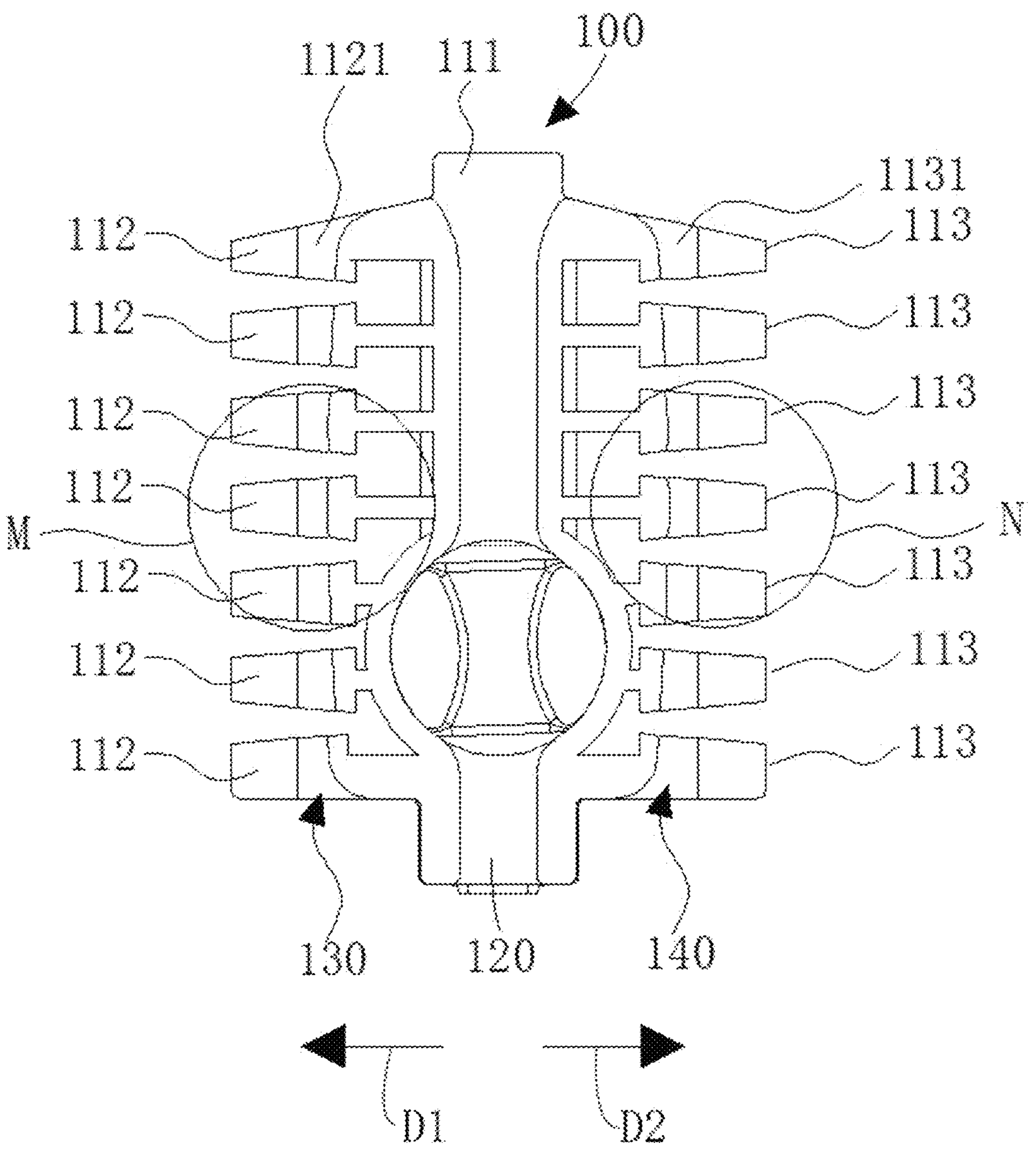
FIG. 6 is a partial cross-sectional view of the surgical stapler according to another embodiment of the present disclosure.
Figure 7:
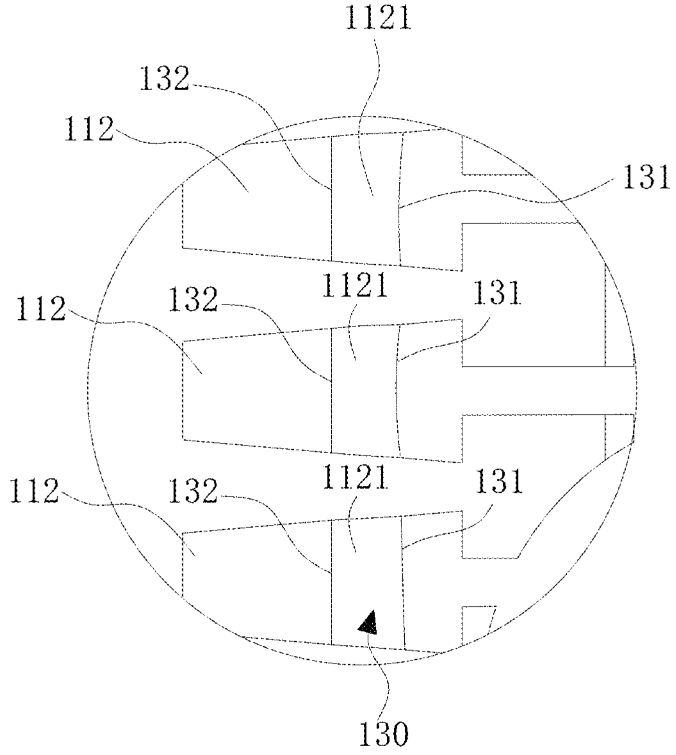
FIG. 7 is an enlarged view of portion M in FIG. 6.
Figure 8:
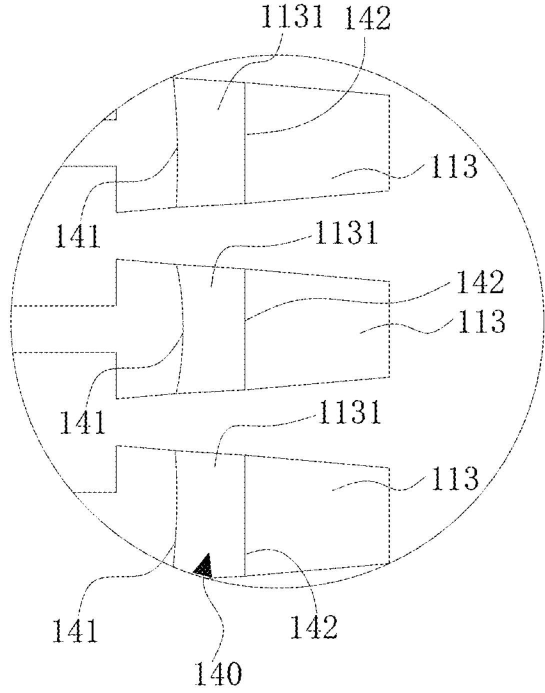
FIG. 8 is an enlarged view of portion N in FIG. 6.

Specifically, as shown in FIG. 6, the intermediate connecting member 100 includes a connecting portion 111 and a plurality of wing portions, with the plurality of wing portions arranged at intervals. It should also be noted that, in some embodiments, the wing portions include a left wing portion 112 and a right wing portion 113. The left wing portion 112 is positioned on the left side of the connecting portion 111, and the right wing portion 113 is positioned on the right side of the connecting portion 111. each left wing portion 112 is formed with its respective first sub-channel 1121, and each right wing portion 113 is formed with its respective second sub-channel 1131. A plurality of first sub-channels 1121 form the first channel 130, and a plurality of second sub-channels 1131 form the second channel 140, with the left wing portions 112 arranged at intervals, and the right wing portions 113 arranged at intervals.

In addition, when the first bending tension member 400 is forced to pull the end effector assembly 200 to bend along a first direction D1, the first bending tension member 400 is positioned on a side of the first channel 130 away from the second channel 140. Such a configuration ensures that the first bending tension member 400 is not affected by the first protruding structure 131, preventing it from being further tightened or generating additional tension force. Thus, the tension force generated by the first bending tension member 400 and the tension force generated by the second bending tension member 500 are kept in balance.

Similarly, when the second bending tension member 500 is forced to pull the end effector assembly 200 to bend along a second direction D2, the second bending tension member 500 is positioned on a side of the second channel 140 away from the first channel 130. Such a configuration ensures that the second bending tension member 500 is not affected by the second protruding structure 141, preventing it from being further tightened or generating additional tension force. Thus, the tension force generated by the first bending tension member 400 and the tension force generated by the second bending tension member 500 are kept in balance.

Specifically, when the first bending tension member 400 is forced to pull the end effector assembly 200 to bend along a first direction D1, the second bending tension member 500 is affected by the second protruding structure 141, while the first bending tension member 400 is not affected by the first protruding structure 131, resulting in the amount of deformation of the first bending tension member 400 being less than the amount of deformation of the second bending tension member 500. Thus, the second bending tension member 500 expands along a second direction D2 to generate additional tension force.

Similarly, when the second bending tension member 500 is forced to pull the end effector assembly 200 to bend along a second direction D2, the first bending tension member 400 is affected by the first protruding structure 131, while the second bending tension member 500 is not affected by the second protruding structure 141, resulting in the amount of deformation of the second bending tension member 500 being less than the amount of deformation of the first bending tension member 400. Thus, the first bending tension member 400 expands along a first direction D1 to generate additional tension force.

Figure 11:
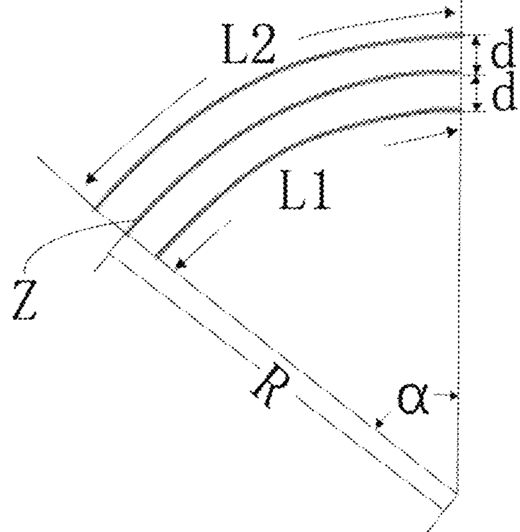
FIG. 11 is a partial schematic view of the surgical stapler according to another embodiment of the present disclosure.
Figure 12:
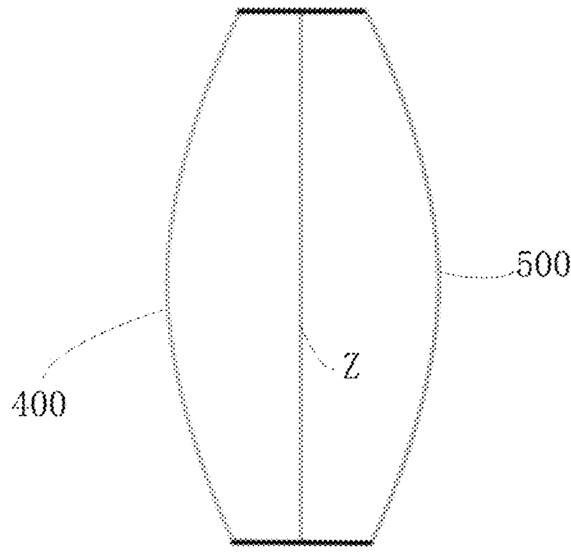
FIG. 12 is a partial schematic view of the surgical stapler according to another embodiment of the present disclosure.

As shown in FIG. 11, it is assumed that the side of the first channel 130 close to the second channel 140 is not provided with the first protruding structure 131, and the side of the second channel 140 close to the first channel 130 is not provided with the second protruding structure 141. When the end effector assembly 200 bends along a first direction D1, the central axis Z of the intermediate connecting member 100, the first bending tension member 400 and the second bending tension member 500 bend around a common center of curvature. The amount of deformation of the first bending tension member 400 is $\Delta L1 = L0 - L1 = R\alpha - (R-d)\alpha = d\alpha$, and the amount of deformation of the second bending tension member 500 is $\Delta L2 = L2 - L0 = (R+d)\alpha - R\alpha = d\alpha$, where $\alpha$ is the central angle, L1 and L2 are the lengths of the first bending tension member 400 and the second bending tension member 500 within the same central angle range, L0 is the length of the central axis Z of the intermediate connecting member 100, R is the distance from the central axis Z of the intermediate connecting member 100 to the center of curvature, and d is the distance from the first bending tension member 400 or the second bending tension member 500 to the central axis Z of the intermediate connecting member 100. Obviously, the amount of deformation of the first bending tension member 400 is equal to the amount of deformation of the second bending tension member 500.

As described herein, the side of the first channel 130 close to the second channel 140 is provided with the first protruding structure 131, and the side of the second channel 140 close to the first channel 130 is provided with the second protruding structure 141. When the end effector assembly 200 bends along a first direction D1, the central axis Z of the intermediate connecting member 100, the first bending tension member 400 and the second bending tension member 500 no longer bend around a common center of curvature, the arc of the second bending tension member 500 shifts outward, resulting in $\Delta L2 > \Delta L1$. Thus, the amount of deformation of the second bending tension member 500 is greater than the amount of deformation of the first bending tension member 400. Conversely, when the end effector assembly 200 bends along a second direction D2, the amount of deformation of the first bending tension member 400 is greater than the amount of deformation of the second bending tension member 500.

Specifically, the outer side wall 132 (i.e., the left side wall) of the first channel 130 is a flat wall, and the outer side wall 142 (i.e., the right side wall) of the second channel 140 is a flat wall. When the intermediate connecting member 100 is in an undeformed state, the outer side wall 132 of the first channel 130 is parallel to the outer side of the first bending tension member 400, and the outer side wall 142 of the second channel 140 is parallel to the outer side of the second bending tension member 500. Such a configuration ensures that when the first bending tension member 400 bends and abuts against the outer side wall 132 of the first channel 130, or the second bending tension member 500 bends and abuts against the outer side wall 142 of the second channel 140, the first bending tension member 400 and the second bending tension member 500 are not further tightened to generate additional tension force.

Figure 9:
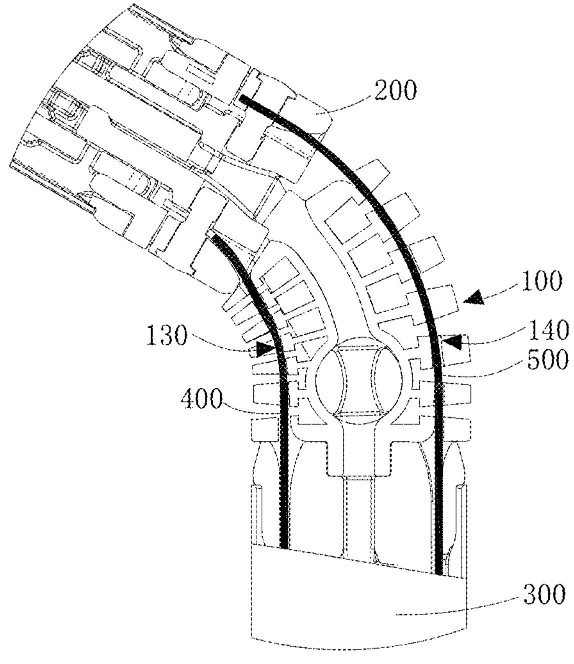
FIG. 9 is a partial cross-sectional view of the surgical stapler according to another embodiment of the present disclosure.

As shown in FIG. 9, when the end effector assembly 200 bends to the left, both the first bending tension member 400 and the second bending tension member 500 bend to the left. The first protruding structure 131 of the first channel 130 is positioned on the right side of the first channel 130, and the outer side wall 132 of the first channel 130 is positioned on the left side of the first channel 130, the outer side wall 142 of the second channel 140 is positioned on the right side of the second channel 140, and the second protruding structure 141 of the second channel 140 is positioned on the left side of the second channel 140. Under this condition, the first bending tension member 400 abuts against the outer side wall 132 of the first channel 130, while the second bending tension member 500 contacts the second protruding structure 141 on the inner side of the second channel 140. Since the outer side wall 132 of the first channel 130 is a flat wall, the first bending tension member 400 is not further tightened. The second protruding structure 141 on the inner side of the second channel 140 protrudes outward, causing the second bending tension member 500 to generate additional tension force.

It should be noted that when the end effector assembly 200 is not bent, the intermediate connecting member 100 extends substantially straight. When the end effector assembly 200 bends, the intermediate connecting member 100 bends toward one side.

In some embodiments, the intermediate connecting member 100 is elastic. When the end effector assembly 200 bends along a first direction D1, the intermediate connecting member 100 is compressed on the side facing the first direction D1 to provide supporting force and stretches on the side facing the second direction D2. When the end effector assembly 200 bends along a second direction D2, the intermediate connecting member 100 is compressed on the side facing the second direction D2 to provide supporting force and stretches on the side facing the first direction D1. Such a configuration enables the intermediate connecting member 100 to support the end effector assembly 200, preventing the end effector assembly 200 from swinging due to resistance during bending. Meanwhile, during bending of the end effector assembly 200, the elastic intermediate connecting member 100 facilitates bending.

In general, the intermediate connecting member 100 is formed with a knife holder channel 120, the knife holder channel 120 is primarily configured to allow the knife holder to pass through and to constrain the position of the knife holder.

Figure 3:
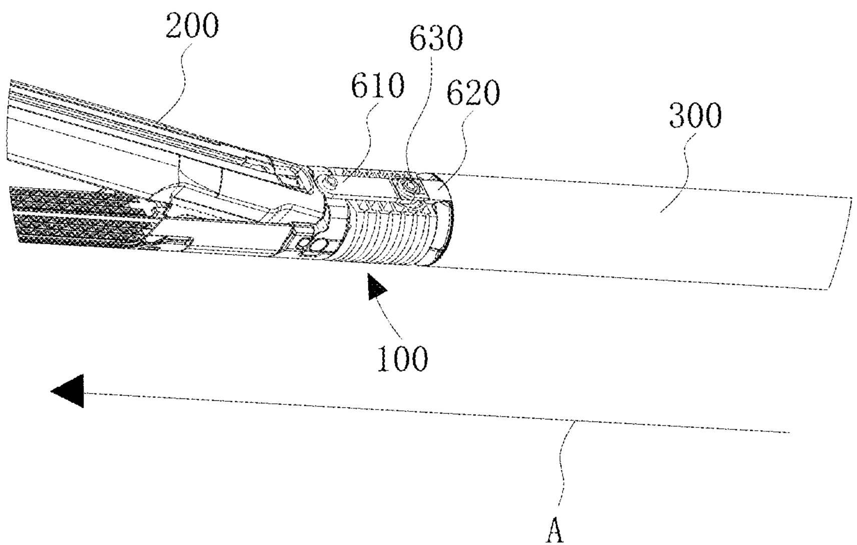
FIG. 3 is a partial perspective view of the surgical stapler according to another embodiment of the present disclosure.
Figure 4:
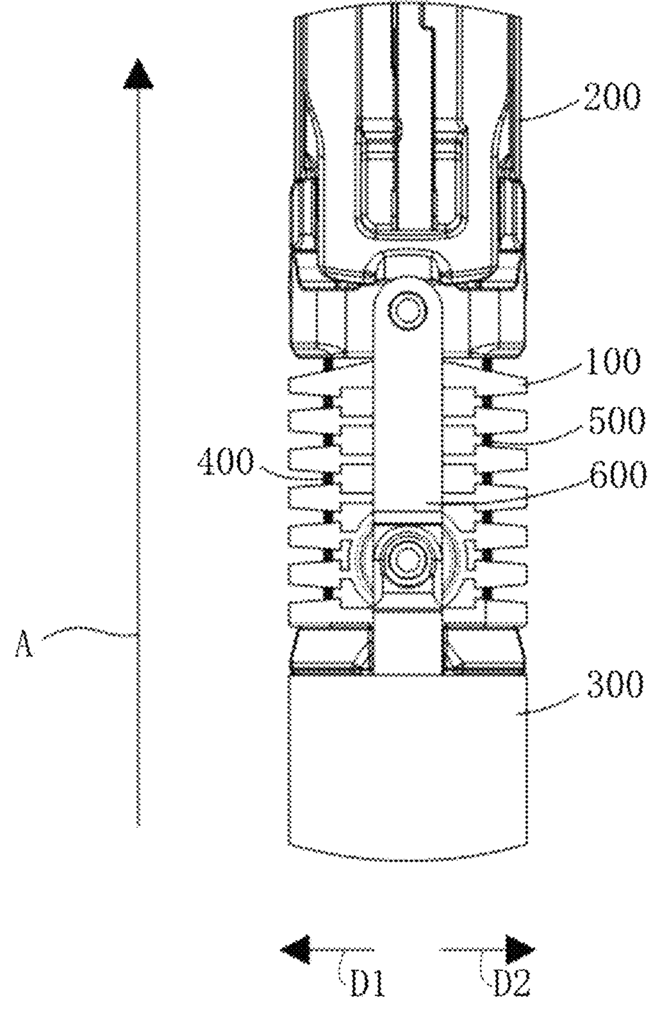
FIG. 4 is a partial top view of the surgical stapler according to another embodiment of the present disclosure.
Figure 5:
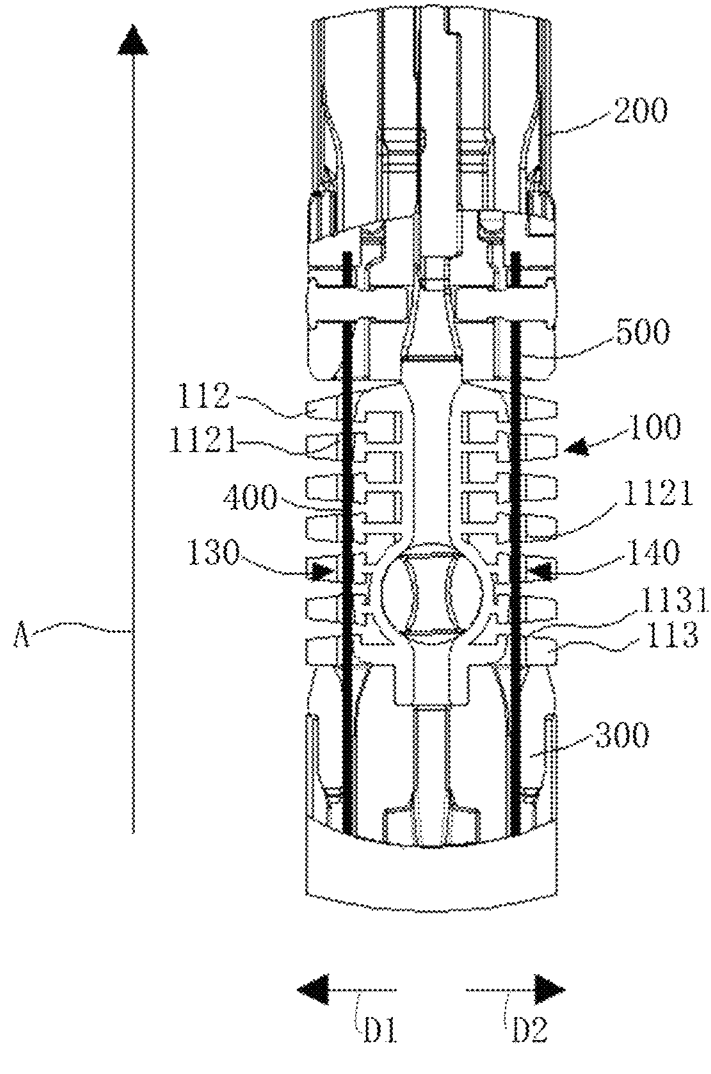
FIG. 5 is a partial cross-sectional view of the surgical stapler according to another embodiment of the present disclosure.

In some embodiments, the connecting tube 300 and the end effector assembly 200 are hingedly connected via an articulated structure 600. Specifically, as shown in FIG. 3, the articulated structure 600 includes a first connecting member 610, a second connecting member 620, and a connecting shaft 630. The first connecting member 610 is mounted on the end effector assembly 200, the second connecting member 620 is mounted on the connecting tube 300, and the first connecting member 610 and the second connecting member 620 are hingedly connected via the connecting shaft 630. Such a configuration enables the bending of the end effector assembly 200 to follow a predetermined path.

In summary, the surgical stapler of the present disclosure includes an intermediate connecting member, an end effector assembly, a first bending tension member, and a second bending tension member. The intermediate connecting member includes a first channel and a second channel. The first bending tension member passes through the first channel to connect to the end effector assembly, and the second bending tension member passes through the second channel to connect to the end effector assembly. The side of the first channel close to the second channel is provided with a first protruding structure. When the second bending tension member is forced to pull the end effector assembly to bend along a second direction, the first bending tension member passively contacts the first protruding structure, expanding along a first direction to generate additional tension force. The present disclosure prevents the first bending tension member from loosening during the surgical procedure, which could cause the end effector assembly to swing, thereby reducing traction or abrasion to the patient's tissue.

In this document, orientations are generally described with reference to the operating physician or the patient of the medical device. The position close to the operating physician of the medical device is referred to as the "proximal end", and the position close to the patient of the medical device is referred to as the "distal end". In addition, the longitudinal direction of the surgical stapler is referred to as the axial direction.

The technical means in the present disclosure are not limited to the technical means disclosed in the preceding embodiments, but also include technical solutions composed of any combination of the preceding technical features. It is to be noted that for those of ordinary skill in the art, a number of improvements and modifications can be made without departing from the principle of the present disclosure, and these improvements and modifications are within the scope of the present disclosure.

What is claimed is:

1. A surgical stapler comprising an intermediate connecting member (100), an end effector assembly (200), a first bending tension member (400), and a second bending tension member (500);

wherein the intermediate connecting member (100) comprises a first channel (130) and a second channel (140);

the first bending tension member (400) is configured to pass through the first channel (130) to connect to the end effector assembly (200); the second bending tension member (500) is configured to pass through the second channel (140) to connect to the end effector assembly (200);

a first protruding structure (131) is provided on a side of the first channel (130) close to the second channel (140);

when the second bending tension member (500) is forced to pull the end effector assembly (200) to bend along a second direction (D2), the first bending tension member (400) passively contacts the first protruding structure (131), expanding along a first direction (D1) to generate additional tension force;

wherein a second protruding structure (141) is provided on a side of the second charmel (140) close to the first channel (130);

when the first bending tension member (400) is forced to pull the end effector assembly (200) to bend along the first direction (D1), the second bending tension member (500) passively contacts the second protruding structure (141), expanding along the second direction (D2) to generate additional tension force;

wherein, when end effector assembly (200) is not bent, the first bending tension member (400) contacts the first protruding structure (131), expanding along the first direction (D1) to generate additional tension force;

the second bending tension member (500) contacts the second protruding structure (141), expanding along the second direction (D2) to generate additional tension force.

2. The surgical stapler according to claim 1, wherein the tension force generated by the first bending tension member (400) and the tension force generated by the second bending tension member (500) are kept in balance.

3. The surgical stapler according to claim 1, wherein the intermediate connecting member (100) is a one-piece structure;

the first channel (130) or the second channel (140) is respectively continuous;

the side of the first channel (130) close to the second channel (140) is integrally formed as the first protruding structure (131);

the side of the second channel (140) close to the first channel (130) is integrally formed as the second protruding structure (141).

4. The surgical stapler according to claim 1, wherein the intermediate connecting member (100) is a multi-piece assembly structure;

the first channel (130) comprises a plurality of first sub-channels (1121);

the second channel (140) comprises a plurality of second sub-channels (1131);

a side of any of the first sub-channels (1121) close to the second sub-channels (1131) is provided with the first protruding structure (131);

a side of any of the second sub-channels (1131) close to the first sub-channels (1121) is provided with the second protruding structure (141).

5. The surgical stapler according to claim 1, wherein, when the first bending tension member (400) is forced to pull the end effector assembly (200) to bend along the first direction (D1), the first bending tension member (400) is positioned on a side of the first channel (130) away from the second channel (140);

when the second bending tension member (500) is forced to pull the end effector assembly (200) to bend along the second direction (D2), the second bending tension member (500) is positioned on a side of the second channel (140) away from the first channel (130).

6. The surgical stapler according to claim 1, wherein, when the first bending tension member (400) is forced to pull the end effector assembly (200) to bend along the first direction (D1), an amount of deformation of the first bending tension member (400) is less than an amount of deformation of the second bending tension member (500);

when the second bending tension member (500) is forced to pull the end effector assembly (200) to bend along the second direction (D2), the amount of deformation of the second bending tension member (500) is less than the amount of deformation of the first bending tension member (400).

7. The surgical stapler according to claim 1, wherein the intermediate connecting member (100) is elastic;

when the end effector assembly (200) bends along the first direction (D1), the intermediate connecting member (100) is compressed on a side facing the first direction (D1) to provide supporting force and stretches on a side facing the second direction (D2);

when the end effector assembly (200) bends along the second direction (D2), the intermediate connecting member (100) is compressed on the side facing the second direction (D2) to provide supporting force and stretches on the side facing the first direction (D1).

8. The surgical stapler according to claim 1, further comprising a handle assembly (11);

wherein the handle assembly (11) comprises a drive assembly;

the first bending tension member (400) and the second bending tension member (500) are respectively connected to the drive assembly;

the drive assembly is configured to tighten the first bending tension member (400) and loosen the second bending tension member (500), thereby driving the end effector assembly (200) to bend along the first direction (D1);

the drive assembly is configured to tighten the second bending tension member (500) and loosen the first bending tension member (400), thereby driving the end effector assembly (200) to bend along the second direction (D2).

9. The surgical stapler according to claim 1, wherein the tension force generated by the first bending tension member (400) and the tension force generated by the second bending tension member (500) are kept in balance.

* * * * *